United States Patent [19]
Stetter et al.

[11] Patent Number: 5,331,310
[45] Date of Patent: Jul. 19, 1994

[54] AMPEROMETRIC CARBON MONOXIDE SENSOR MODULE FOR RESIDENTIAL ALARMS

[75] Inventors: Joseph R. Stetter, Naperville; Li Pan, Lisle, both of Ill.

[73] Assignee: Transducer Research, Inc., Naperville, Ill.

[21] Appl. No.: 864,330

[22] Filed: Apr. 6, 1992

[51] Int. Cl.$^5$ ............................................. G08B 17/10
[52] U.S. Cl. .................................. 340/632; 340/628; 204/406
[58] Field of Search ............... 340/628, 629, 632, 633, 340/634; 204/406, 410, 411, 412, 424; 324/438, 439, 425; 73/23.31

[56] References Cited

U.S. PATENT DOCUMENTS

| | | | |
|---|---|---|---|
| 3,776,832 | 12/1973 | Oswin et al. | 204/412 X |
| 4,171,253 | 10/1979 | Nolan et al. | 204/412 X |
| 4,688,021 | 8/1987 | Buck et al. | 340/632 X |
| 4,767,994 | 8/1988 | Hopkins et al. | 324/438 |
| 4,874,500 | 10/1989 | Madou et al. | 204/412 |

*Primary Examiner*—Jeffery A. Hofsass
*Attorney, Agent, or Firm*—Solomon Zaromb

[57] ABSTRACT

A relatively inexpensive modular component that can be substituted for, or used in conjunction with, an existing smoke detector in a commercially available residential fire-detection alarm comprises: (A) an amperometric sensor for carbon monoxide, in which the reference and counter electrodes are combined either internally into a single auxiliary electrode or externally by electrical shorting; and (b) a simple current-to-voltage converter circuit that converts the current signals from the sensing electrode into amplified voltage signals. The converter circuit is powered by the same battery (usually a 9-volt dry cell) and is connected to the same alarm-triggering circuit that are used in existing residential fire alarms. The sensor-and-converter module is designed to fit into a commercially available smoke-detector-type fire alarm unit. The electrical output of the module is designed to be compatible with the electrical input requirements of the commercial detection circuitry. An alarm fitted with this module provides early warning of hazardous conditions, such as a smoldering fire, a leaky furnace, or an otherwise heavily polluted atmosphere.

20 Claims, 6 Drawing Sheets

AMPEROMETRIC CARBON MONOXIDE SENSOR MODULE FOR RESIDENTIAL ALARMS

BACKGROUND OF THE INVENTION

This invention relates to a simple and inexpensive sensor module for use in residential alarms.

Devices for sensing carbon monoxide and triggering an alarm in the presence of excessive concentrations of carbon monoxide (CO) that may be hazardous to life or health are presently available for many industrial applications, but such devices are still too costly for use in most homes. These devices may utilize electrochemical sensors, semiconductor sensors, colorimetric detectors or IR (infra-red) detectors. Typical electrochemical industrial alarms have the potential to be used in homes because of their excellent sensitivity and selectivity. The electrochemical alarms may be preferred to the semiconductor sensors because the semiconductor must be heated and therefore utilize significant power which limits battery life or requires drawing current from the residential power line (e.g., via a plug in a wall receptacle or permanent wiring of the alarm into the house). Infra-red detectors of CO are expensive and bulky, requiring a long path length, heated IR sources, and expensive detectors. Further, the present lower detection limit of semiconductor sensors may be 10 to 100 times higher than that of electrochemical sensors. Typical sensitivity ranges are 50–200 ppmv (parts per million by volume) for semiconductor sensors and 0.1–100 ppmv for electrochemical sensors. Other CO detectors, e.g., those of the colorimetric type, also lack sensitivity and/or reversibility or accuracy or convenient output to trigger an alarm.

The current trend is towards a reduction in the maximum permissible CO levels. The older limits set by the Occupational Safety and Health Administration are 50 ppmv over an eight-hour period and 400 ppmv for 15 minutes in workplace atmospheres. However, a concentration limit set by the Environmental Protection Agency is as low 9 ppmv CO for the outdoor atmosphere.

Ideally, a home should have only background CO present and this may be very low, near to 0 ppmv in the countryside or 1-2 ppmv in the city or close to combustion sources. A reading of 9 ppmv is indicative of a problem with the indoor air quality. Indeed, even a reading of 4 ppmv has been found to indicate potential problems. Therefore it is important to have a sensitive detector that will alarm at low levels.

It is therefore one object of this invention to provide an indoor hazard-warning device that will alarm at a preselected CO level in the range of 4-20 ppmv of CO in air or possibly even lower, if required. The preferred alarm level may depend on future evaluations of the health effects of CO on humans and of the levels of CO that may be indicative of other hazardous conditions, such as a smoldering fire or a leaky furnace.

It is a further object of this invention to provide such a hazard-warning device in a form that is inexpensive and adaptable for insertion into a typical residential smoke alarm. This implies that the device must be small, powered by a small battery, and drawing a current that is sufficiently low to assure longevity of the battery.

The heating that is required for the operation of a semiconductor-type sensor may pose a potential fire hazard. It is therefore another object of this invention to provide a CO-sensing device in a form that is intrinsically safe for home use. This implies that the device must not require heating or have otherwise hazardous features.

The responses of semiconductor-type or of colorimetric sensors to increased concentrations of carbon monoxide are much slower than those of electrochemical sensors. It is therefore still another object of this invention to provide a warning device that responds rapidly to the presence of elevated levels of carbon monoxide.

It is necessary to test warning devices periodically and verify that they function properly. This introduces the problem of reversibility. Colorimetric devices either do not revert to their original state after exposure to a test sample or do so very slowly. Semiconductor sensors also require a long time to reset. In contrast, electrochemical sensors revert to their zero background responses shortly after the CO concentration drops to zero. It is therefore yet a further object of this invention to provide a CO-alarming device that can be conveniently tested and thereafter quickly reset for normal operation.

Although it is clear from the foregoing discussion that electrochemical sensors offer important advantages over semiconductor-type, colorimetric, or IR detectors for CO alarms, there is still the problem of the relatively high cost and complexity of present electrochemical CO-monitoring devices. These industrial devices utilize amperometric two-electrode or, most often, three-electrode sensors that comprise a CO-sensing electrode, a counter electrode, and a reference electrode and yield a current that is proportional to the concentration of carbon monoxide in the ambient air.

To assure good accuracy and stability, the potential of the sensing electrode is kept fixed relative to that of the reference electrode by means of a potentiostat circuit that also serves to measure the sensor current. The complexity and cost of the sensor and of the potentiostat circuit presently limit the use of electrochemical CO sensors to industrial applications only. The complex circuit serves to reduce noise and provides amplification and signal conditioning for outputs to displays, relays and computers. Many circuits also need to compensate for the effects of temperature fluctuations on the signal.

It is therefore yet another object of this invention to provide an electrochemical sensor and a simplified current-measuring circuit that is inexpensive and readily adaptable for use in existing home or other residential fire alarms.

SUMMARY OF THE INVENTION

Briefly, the invention consists of an inexpensive modular component that can be substituted for, or used in conjunction with, an existing smoke detector or ionization detector in one of the commercially available mass-produced residential fire detection and alarm units. The modular component comprises (a) an amperometric sensor for carbon monoxide, in which the reference and counter electrodes are combined either internally into a single auxiliary electrode or externally by electrical shorting, and (b) a simple current-to-voltage converter circuit that converts the current signals from the sensing electrode into amplified voltage signals. The converter circuit is powered by the same battery (usually a 9-volt dry cell) and is connected to the same alarm-triggering circuit that are used in existing residential fire alarms. The sensor-and-converter module is designed to fit into a commercially available smoke-detector-type fire alarm unit. The electrical output of the module is designed to be compatible with the electrical input requirements of the commercial detection circuitry. An alarm fitted with this module provides early warning of hazardous conditions, such as a smoldering fire, a leaky furnace, or an otherwise heavily polluted atmosphere.

BRIEF DESCRIPTION OF THE DRAWINGS

The invention is best explained with reference to the drawings, in which.

DESCRIPTION OF THE PREFERRED EMBODIMENT

Figure 1:
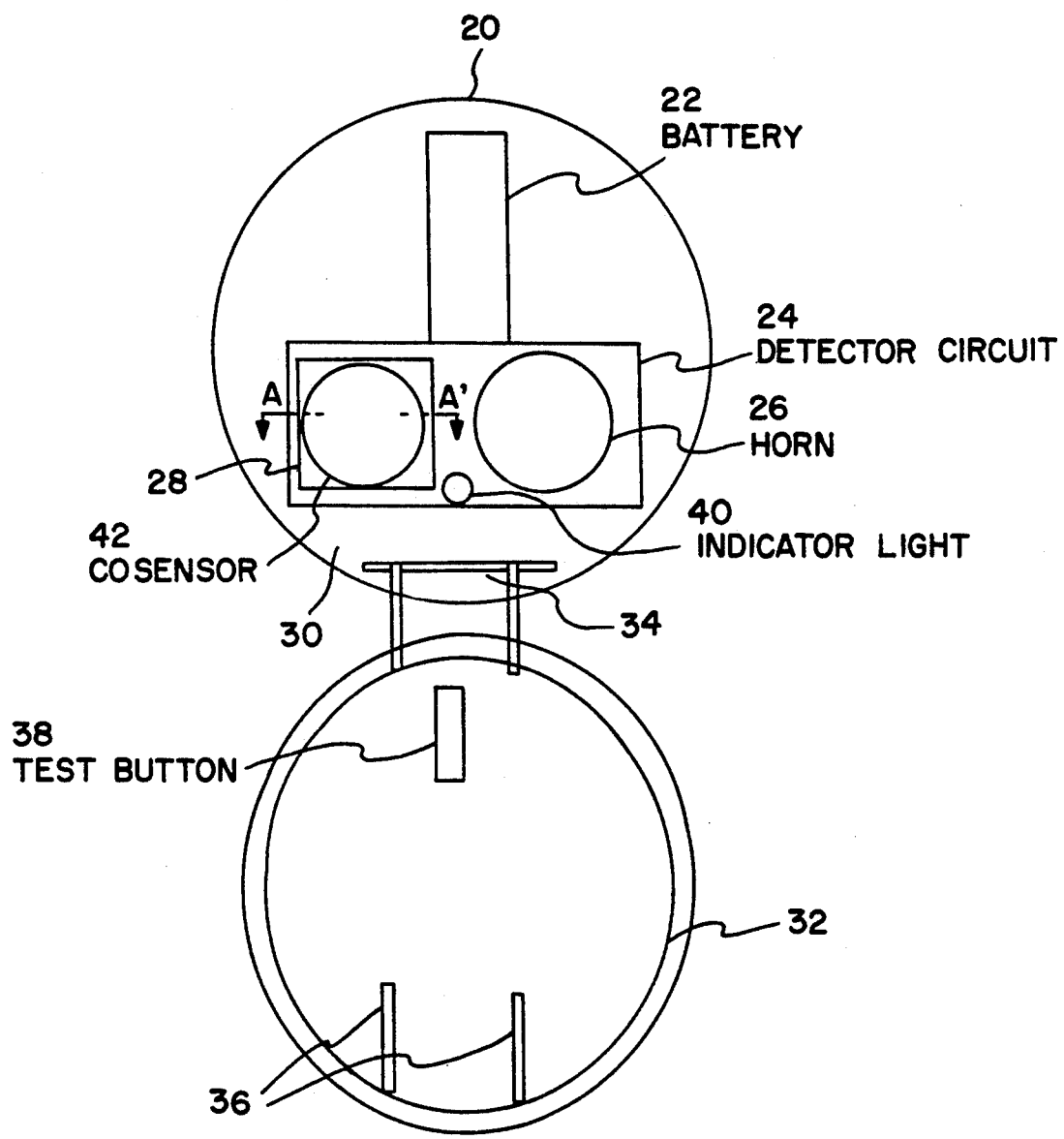
FIG. 1 is a bottom view of a typical, mass-produced, commercially available, residential smoke detector with an unlatched cover, wherein a module comprising an amperometric CO sensor and a current-to-voltage converter circuit has been substituted for the original smoke detector.

FIG. 1 is a schematic bottom view of a typical, mass-produced, commercially available, residential smoke alarm 20, powered by a 9-volt battery 22, and comprising a detector circuit board 24, onto which are affixed an alarm horn 26, and a CO sensor and converter circuit module 28, which replaces the original smoke detector (not shown). Battery 22 and circuit board 24 are affixed onto a detector base 30. A detector cover 32 is attached to base 30 by means of a hinge 34 which permits it to be swung open as shown or swung shut with the aid of latches 36. A test button 38 and an optional indicator light 40 serve to verify the functionality of the CO alarm.

Figure 2:
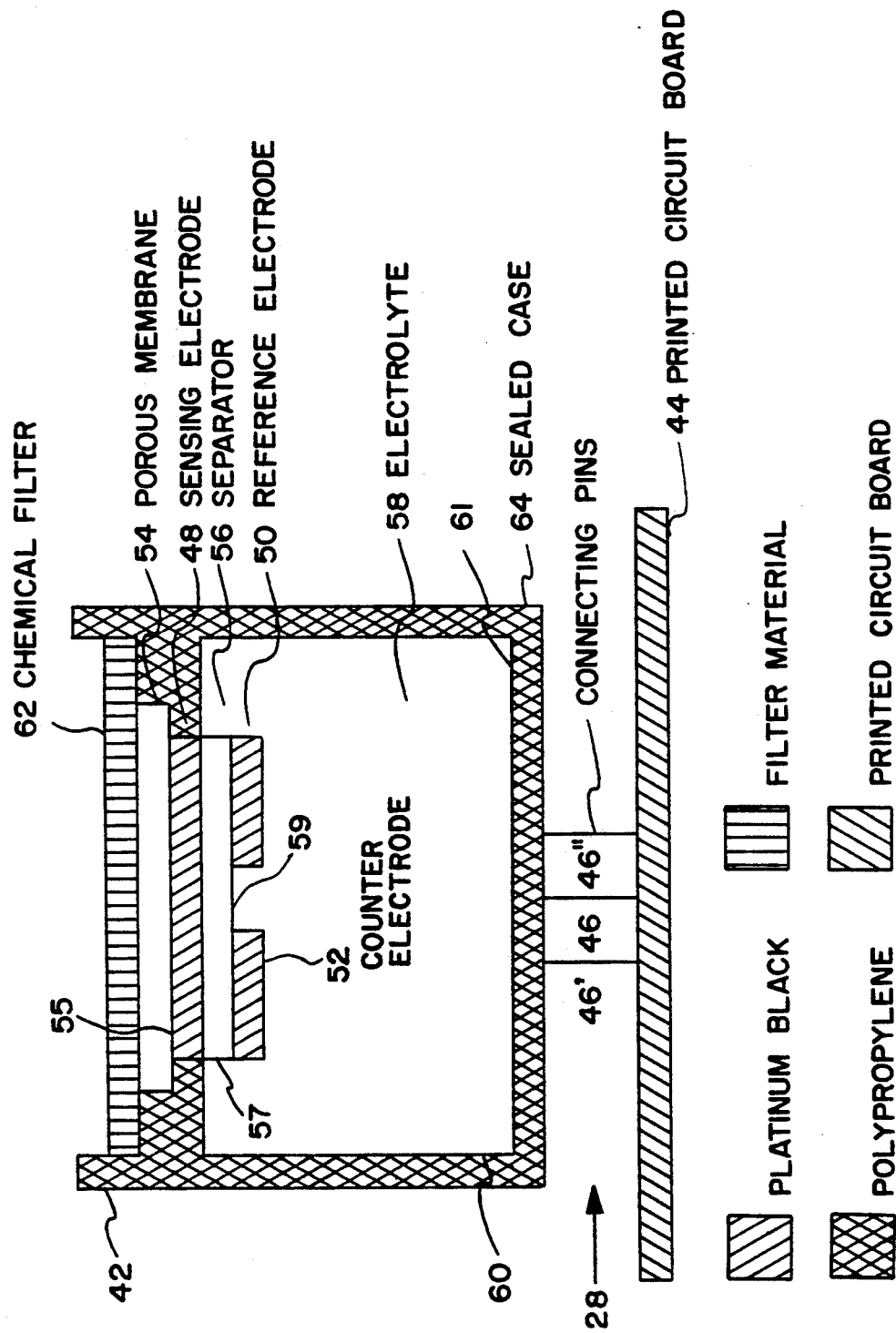
FIG. 2 is a view of Section A—A' of the module of FIG. 1.

As shown in the magnified cross-sectional view of FIG. 2, module 28 comprises a CO sensor 42 that is electrically connected to a circuit board 44 through pins 46, 46' and 46''. Pin 46 is connected inside sensor 42 to the sensing electrode 48, whereas pins 46' and 46'' are connected to the reference electrode 50 and the counter electrode 52, respectively. Sensing electrode 48, comprising a layer of platinum black mixed with a hydrophobic polytetrafluoroethylene binder, is contacting a gas-permeable electrolyte-impermeable porous polytetrafluoroethylene membrane 54 on its upper side 55 and a separator 56 on its lower side 57. Separator 56, made of an electrically insulating, highly porous, hydrophilic material, is contacted at its lower surface 59 by the reference and counter electrodes 50 and 52, both of which also comprise platinum black. The electrically insulating property of the separator material prevents electronic conductivity between the three electrodes 48, 50, and 52 within sensor 42. However, thanks to the hydrophilicity of its pores, separator 56 is soaked with the cell electrolyte 58, thereby assuring good ionic conductivity between these electrodes. A part of separator 56, not shown in cross-section, extends to the base 61 of the electrolyte chamber 60, thereby assuring that the separator remains soaked, through a wicking action, even when the electrolyte level drops well below the surface 59.

The operation of sensor 42 is based on the electrochemical oxidation of CO at the sensing electrode 48. To prevent false alarms due to other oxidizable compounds that may be generated from cooking, such as nitric oxide, nitrogen dioxide, alcohols or aldehydes, a chemical filter 62 that reacts with such possibly interfering compounds, is interposed between the ambient air and the gas-permeable membrane 54. This assures that sensor 42 responds solely to CO. Filter 62 may comprise a mixture of charcoal or activated carbon, potassium permanganate, and/or other adsorbents and reactants that can eliminate unwanted gases from entering the sensor. Many examples are found in the art of filters and chemical reagents on charcoal cloth or filter paper that can remove chemical contaminants and enhance the air-cleaning properties of this type of filter.

The electrolyte 58 is contained in a tightly sealed case 64, made of polypropylene or other electrically insulating, readily machinable or moldable, electrolyte-impervious material. It is of utmost importance that case 64 with membrane 54 form an absolutely leakproof enclosure, as the electrolyte 58 may comprise highly corrosive sulfuric acid, so that any likelihood of electrolyte leakage would render sensor 42 unsuitable for residential use.

Figure 3:
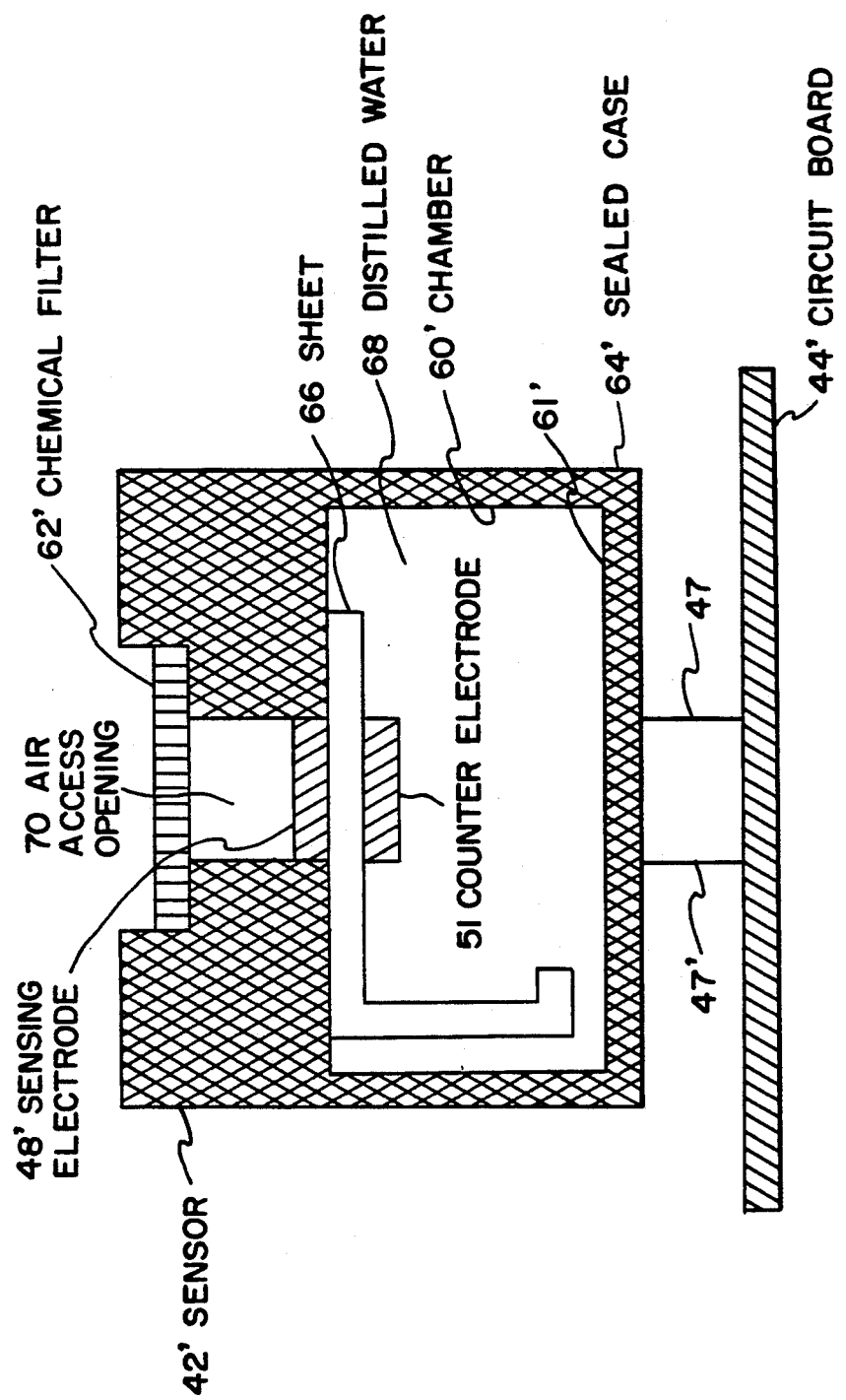
FIG. 3 is the view of the same Section A—A' of an alternative module of FIG. 1.

To eliminate any possibility of corrosive electrolyte leakage, an alternative sensor 42' is shown in the magnified cross-sectional view of FIG. 3. In this embodiment of the invention, a single counter electrode 51, also referred to as auxiliary electrode, faces the sensing electrode 48'. Pins 47 and 47' are connected within sensor 42' to electrodes 48' and 51 and externally to circuit board 44'. Furthermore, an ionically conductive sheet 66, made of polytetrafluoroethylene sulfonic acid (Nafion)——a room-temperature solid electrolyte——replaces the separator 56 of FIG. 2. However, in order to remain ionically conductive, the Nafion must be wetted with water. Therefore, chamber 60' is filled with distilled water 68, and sheet 66 extends all the way down to the bottom 61' of chamber 60' to insure wetting of the Nafion, through a wicking action, even when the bulk of the water 68 fails to make direct contact with the auxiliary electrode 51.

To prevent excessive loss of water through evaporation, the sealed case 64' has an air access opening 70 that is much narrower than that provided for the porous membrane 54 of FIG. 2. Consequently, the areas of the sensing electrode 48' and of the chemical filter 62' are much smaller than those of the corresponding components 48 and 62 of FIG. 2.

Alternative amperometric CO sensors may be obvious to those skilled in the art. Such sensors can be constructed with nonaqueous, preferably gelled, electrolytes, or with other noble metal and metallo-organic catalysts or with other auxiliary or reference electrodes.

Figure 4:
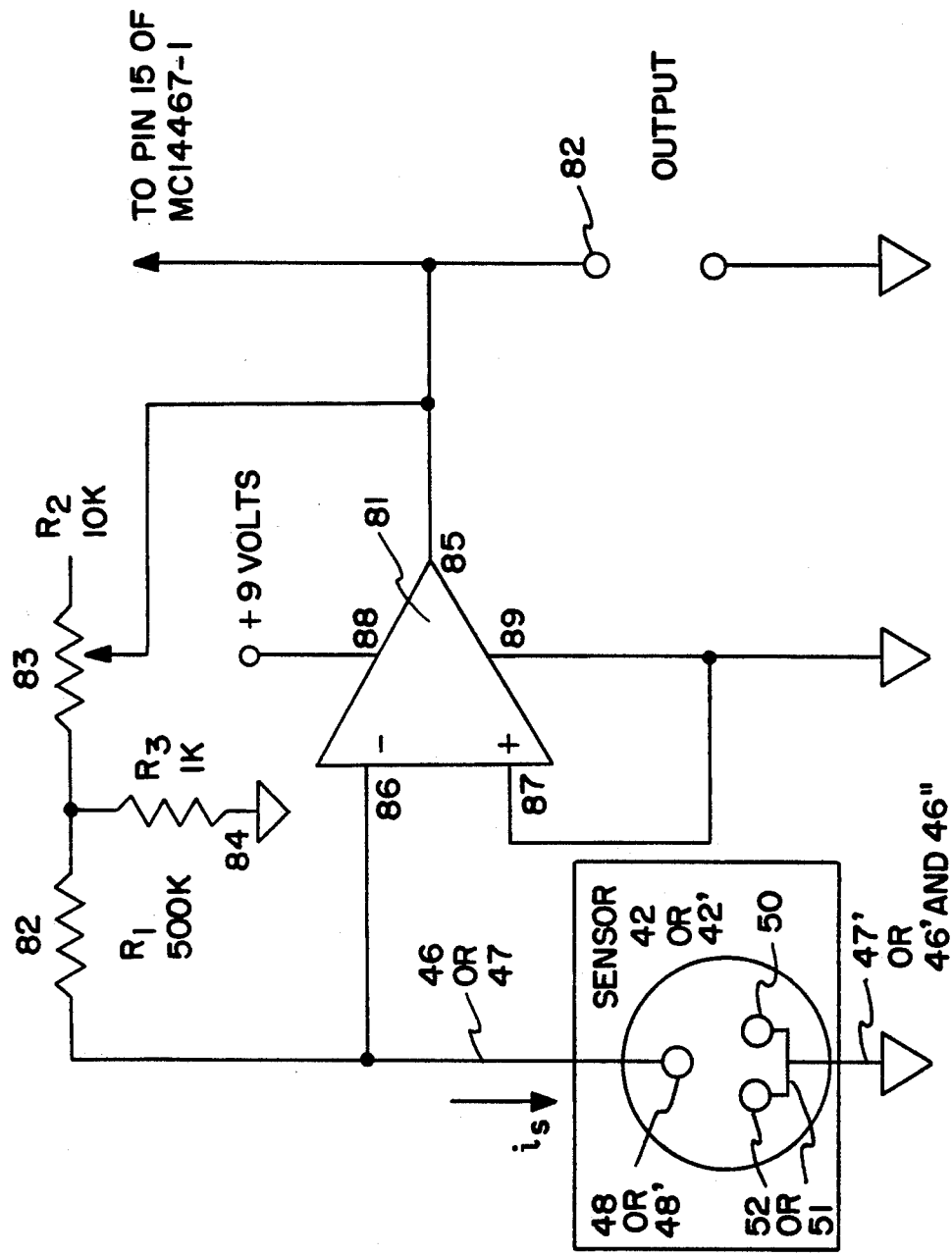
FIG. 4 is a circuit diagram of the converter of FIGS. 1 and 2 or 3.

The board 44 or 44' of FIG. 2 or 3 includes the circuit shown in FIG. 4. Also shown in FIG. 4 are the electrodes 48, 50 and 52 for the sensor of FIG. 2 or 48' and 51 for that of FIG. 3 and the corresponding pin connections 46 and 46'-46'' or 47 and 47'. This circuit has been designed for adequate performance with a minimum number and minimum cost of parts, thus greatly simplifying the practical commercial manufacture. The typical circuit used to operate amperometric gas sensors is much more complex and is used to maintain a constant potential between the reference and working electrodes. A carbon monoxide sensor whose working and reference electrodes contain platinum black may be operated at an applied bias potential of 0 volts between the sensing electrode 48 and the reference electrode 50. The circuit of FIG. 4 accomplishes the same purpose, because the reference electrode of the sensor is connected directly to ground, and the working electrode is held at a voltage very close to ground by the dynamic operation of the circuit. Hence the potential of the working electrode, relative to the reference electrode, is very near zero.

When CO is oxidized at the sensing electrode 48 (or 48'), a negative current is generated in the direction of pin 46 (or 47), the inverting input 86 of the operational amplifier 81, and the resistors 82, 83, and 84. The integrated-circuit operational amplifier 81 is configured as a current-to-voltage converter. The three resistors R1 (82), R2 (83), and R3 (84) constitute a feedback circuit. They are connected in such a way as to emulate a single resistor of much higher resistance. This makes it possible to avoid the use of high-value variable resistance components that are expensive and unstable. The positive voltage $V_o$ that appears at the output 82 of the operational amplifier is proportional to the current $i_s$ from the sensor 42 (or 42') according to the relationship:

$$V_o = i_s(R_1R_2 + R_2R_3 + R_1R_3)/R_3 \quad (1)$$

For the preferred resistance values that are indicated in FIG. 4, $R_1 = 500,000$ ohms, $R_2 \leq 10,000$ ohms, and $R_3 = 1,000$ ohms, Equation 1 yields $V_0 \leq 5.51$ volts for $i_s = 1$ μA. Since the current output of amperometric CO sensors is usually in the range of 0.1–1 μA/ppmv CO, the amplification obtained with the circuit of FIG. 4 can be seen to be fully adequate for residential alarm purposes. Of course, minor modifications to the circuit would be obvious to accommodate sensors whose output falls outside the range of 0.1–1 μA/ppmv.

Figure 6:
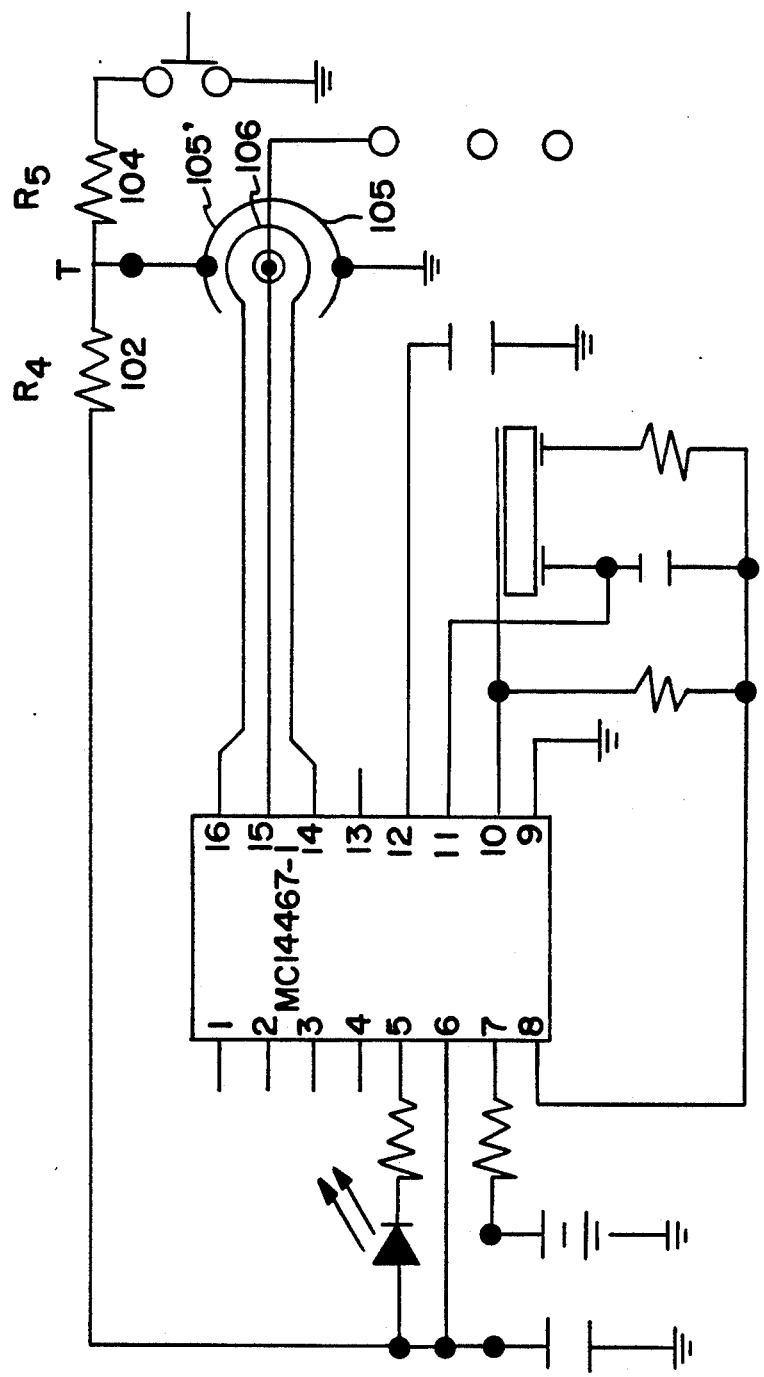
FIG. 6 is a diagram of a typical fire alarm circuit to which the circuit of FIG. 4 is interconnected.

The output $V_0$, relative to ground, can be measured with a volt meter for testing purposes or it can be carried to the input (pin 15 of MC 14467-1) of a smoke detector circuit, such as that shown in FIG. 6.

Other necessary connections of the operational amplifier must be made for correct operation. The circuit is powered by a 9-volt dry cell through connections 88 and 89. The non-inverting amplifier input 87 must be connected to ground. It is important that the operational amplifier 81 be of a type in which the input voltages can closely approach the voltage of the negative battery or power supply terminal (which is ground in this instance). The Part No. TLC271 (supplied by Texas Instruments, Austin, Tex.) is an example of this type of operational amplifier.

Figure 5:
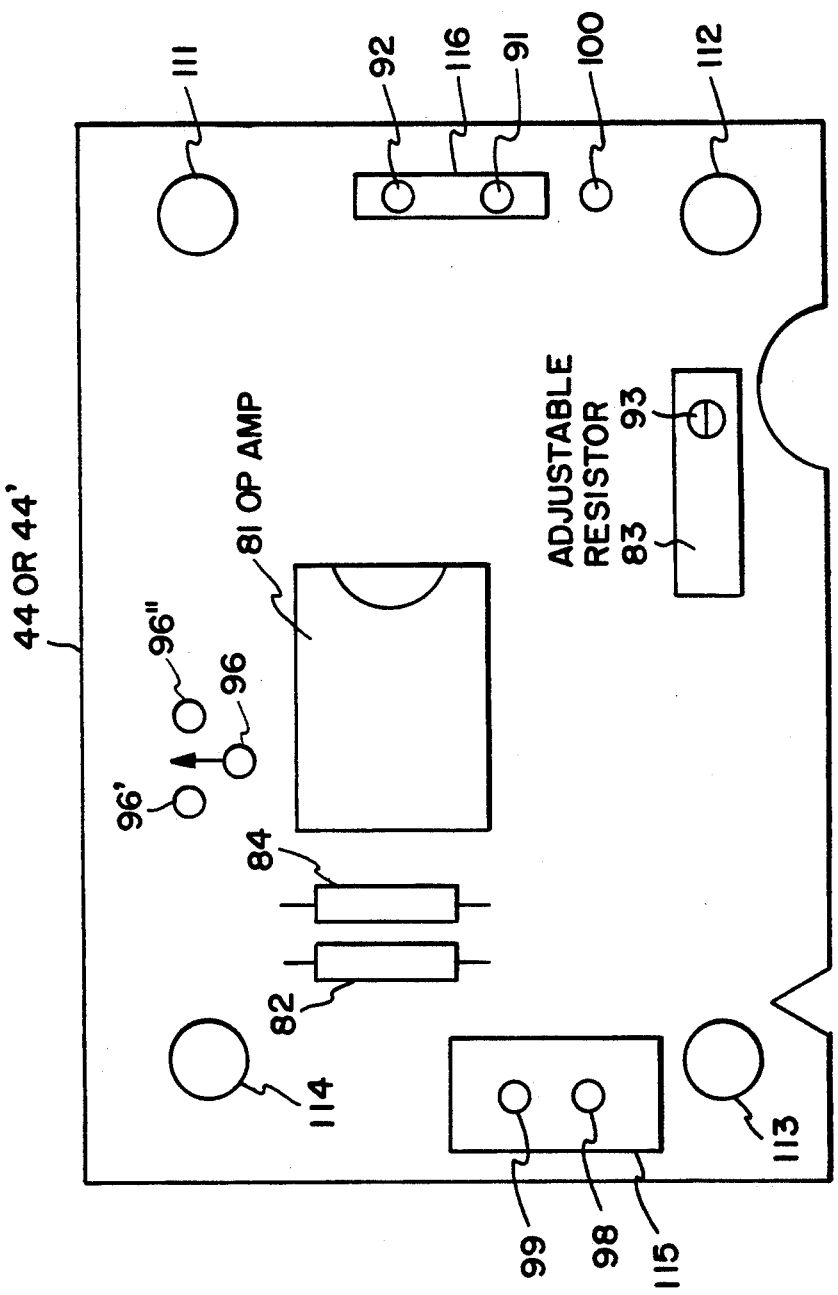
FIG. 5 is a layout of the elements of the circuit of FIG. 4.

A preferred layout of the circuit components of FIG. 4 on board 44 (of FIG. 1) or 44' (of FIG. 3) is shown in FIG. 5. The adjustable resistor 83 is placed near the rim of the board for easy access to its adjusting screw 93. Three tiny receptacles 96, 96', and 96" are provided for insertion of sensor pins 46 (or 47), 46' (or 47'), and 46" (or none), respectively. Terminals 91 and 92 affixed to an insulating support 116 are provided for checking the output of the converter module. Terminals 98 and 99 affixed to an insulating support 115 are provided for connections to the positive and negative terminals, respectively, of a 9-volt dry cell that usually serves to power a residential smoke alarm system. Holes 111, 112, 113, and 114 are provided for the board to be held in place bolts or screws. Also provided is a terminal 100 for connection to pin 15 of the integrated circuit (Motorola) MC14467-1 of FIG. 6.

In FIG. 6, the output of the simple circuit of FIG. 4 is connected to the input of the integrated circuit MC14467-1 at pin 15. Guard rings are connected to pins 14 and 16 so that small currents can be measured without electrical interference. Thus CO sensors of lower output than those given in the following Example 1 can be designed and used with this circuit. Other parts of the circuit of FIG. 6 are already known to provide low battery indication and audio or visual alarm functions. The resistance values $R_4$ and $R_5$ of the respective resistors 102 and 104 in FIG. 6 are chosen to be suitable for the particular application, with 500 kΩ–1 MΩ being typical values. Further, direct connections of the analog signal (bypassing the guard rings (105', 105, and 106) illustrated in FIG. 6) to pin 15 is possible. Also, a simple jumper or switch can be used to silence the alarm during QA/QC testing and setup and this modification is a procedure of convenience that can be easily used by those skilled in the art.

Of course, other circuits are known in the art that can provide simple operation and alarm capability and other conveniences such as those described above. Those described above were selected because they provide a device that is easily calibrated, maintenance free, and relatively inexpensive and they require few modifications to existing technology to achieve a significant new capability.

The following example illustrates the performance of a typical module of this invention:

EXAMPLE 1

The output voltage of a sensor module of the type shown and described in conjunction with FIGS. 2 and 4 was measured at 0° C., 25° C. and 40° C. upon exposure to air and to 20 ppmv of CO. The results are summarized in Table 1.

TABLE 1

Effect of Temperature on the Background and Output Voltages of a CO Sensor Module

| Temperature (°C.) | Output Voltage (V) Upon Exposure to | |
|---|---|---|
| | Pure Air | 20 ppmv CO |
| 0 | 0.22 | 3.72 |
| 25 | 0.35 | 5.20 |
| 40 | 0.55 | 6.50 |

Therefore, according to Table 1, regardless of the ambient temperature, a triggering voltage of 3.5 V will set off an alarm when the CO concentration is in the range of 10–20 ppmv but not when the CO concentration is below that range.

The same module was provided with a chemical filter comprising activated charcoal (made by Cabot Carbon Corporation) and its measured response to various potentially interfering gas mixtures was found to be as listed in Table 2.

TABLE 2

Responses of CO Module to Potential Interferences

| Interference | Concentration | Response (V) |
|---|---|---|
| laboratory air | — | 0.35 |
| hydrogen sulfide | 100 | 0.62 |
| sulfur dioxide | 100 | 0.20 |
| ammonia | 100 | 0.45 |
| alcohol | 100 | 0.85 |
| gasoline | 500 | 0.81 |

TABLE 2-continued

| Responses of CO Module to Potential Interferences | | |
|---|---|---|
| Interference | Concentration | Response (V) |
| carbon dioxide | 1,000 | 0.33 |
| natural gas | 10,000 | 4.67 |
| cigarette smoke | — | 8.16 |

According to Table 2, only cigarette smoke generated directly next to the sensor module or natural gas in the dangerously high concentration of 1% (not far from the 5% explosion threshold) would generate a triggering voltage in excess of 3.5 V.

In an alternative embodiment of the invention, the circuits of FIGS. 4 and 6 may be combined into a single module.

There will now be obvious to those skilled in the art many modification or variations of the afore-disclosed embodiments which, however, shall remain within the scope of the invention if defined by the following claims.

We claim:

1. A modular component that is adaptable for use in a residential smoke detector alarm so as to permit detection of hazardous or hazard-indicating concentrations of carbon monoxide in air, comprising:
   an amperometric sensor having a sensing electrode for detecting carbon monoxide in air and a counter-electrode;
   and a current-to-voltage converter circuit that converts the current flowing from said sensing electrode to a voltage signal,
said converter circuit being adaptable to a smoke-detector integrated circuit that converts a voltage signal in excess of a predetermined level into a trigger signal for actuating an alarm.

2. The component of claim 1, wherein said sensor comprises a reservoir of water or of an electrolyte contained in a tightly sealed chamber and an especially narrow air access opening that prevent excessive loss of water by evaporation.

3. The component of claim 2, wherein said electrolyte comprises sulfuric acid.

4. The component of claim 2, wherein said electrodes are disposed on a water-insoluble solid ionic conductor.

5. The component of claim 4, wherein said ionic conductor is a polymer comprising sulfonic acid groups in its molecular chains.

6. The component of claim 5, wherein said polymer is fluorinated.

7. The component of claim 6, wherein said ionic conductor comprises polytetrafluoroethylene sulfonic acid.

8. The component of claim 2, wherein said sensor comprises a chemical filter for removing compounds that may be mistaken for carbon monoxide.

9. The component of claim 8, wherein said filter comprises carbon and a permanganate salt.

10. The component of claim 1, wherein said converter circuit comprises an operational amplifier and a feedback circuit.

11. The component of claim 10, wherein:
   said operational amplifier has one inverting and one non-inverting input, the non-inverting input being connected directly to the negative terminal of a battery;
   said counter electrode is connected to said non-inverting input; and
   said sensing electrode is connected to said inverting input.

12. The component of claim 11, wherein said amplifier has an output connection and said feedback circuit comprises a first, second, and third resistor, said first resistor being connected at one of the ends to said inverting input and at its other end to each of said second and third resistors, said second resistor being connected at one of its ends to each of said first and third resistors and at its other end to said non-inverting input; and said third resistor being connected at one of its ends to each of said first and second resistors and at its other end to said output of the amplifier.

13. The component of claim 12, wherein said third resistor has an adjustable resistance.

14. Apparatus for detecting excessive concentrations of carbon monoxide in air comprising a modular component that is small enough to be fitted into and be otherwise adaptable for use in a residential smoke detector alarm, said modular component comprising:
   an amperometric sensor having a sensing electrode and a counter-electrode, and
   a current-to-voltage converter circuit that converts the current flowing from said sensing electrode to a voltage signal,
   said converter circuit being adaptable to a smoke-detector integrated circuit that converts a voltage signal in excess of a predetermined level into a trigger signal for actuating an alarm.

15. The apparatus of claim 14, wherein said converter circuit comprises an operational amplifier and a feedback circuit.

16. The apparatus of claim 15, wherein:
   said operational amplifier has one inverting and one non-inverting input, the non-inverting input being connected directly to the negative terminal of a battery;
   said counter electrode is connected to said non-inverting input; and
   said sensing electrode is connected to said inverting input.

17. The apparatus of claim 16, wherein said amplifier has an output connection and said feedback circuit comprises a first, second, and third resistor, said first resistor being connected at one of its ends to said inverting input and at its other end to each of said second and third resistors, said second resistor being connected at one of its ends to each of said first and third resistors and at its other end to said non-inverting input; and said third resistor being connected at one of its ends to each of said first and second resistors and at its other end to said output of the amplifier.

18. The component of claim 17, wherein said third resistor has an adjustable resistance.

19. A method of producing an apparatus for detecting hazardous or hazard-indicative concentrations of carbon monoxide which comprises the step of connecting a modular amperometric carbon monoxide sensor that is adaptable for use in a residential smoke detector with a current-to-voltage converter circuit connected to the existing alarm circuit of the residential smoke detector.

20. The method of claim 19 comprising the preliminary step of removing the smoke detector from a residential fire detector so as to permit substitution therefore of a module comprising an amperometric carbon monoxide sensor with a current-to-voltage converter.

* * * * *